United States Patent [19]

Wierzbicki et al.

[11] Patent Number: 5,128,367
[45] Date of Patent: Jul. 7, 1992

[54] DIVALENT METAL SALTS OF 2-(N-N-DI(CARBOXYMETHYL)AMINO)-3-CYANO-4-CARBOXYMETHYLTHIOPHENE-5-CARBOXYLIC ACID

[75] Inventors: Michel Wierzbicki, Etang la Ville; Jacqueline Bonnet, Paris; Martine Brisset, Caen; Yannis Tsouderos, La Celle Saint Cloud, all of France

[73] Assignee: Adir et Compagnie, France

[21] Appl. No.: 576,225

[22] Filed: Aug. 31, 1990

[30] Foreign Application Priority Data

Sep. 1, 1989 [FR] France ................. 89 11475

[51] Int. Cl.$^5$ .................... A61K 31/38; C07D 333/38
[52] U.S. Cl. ........................ 514/447; 549/61
[58] Field of Search .................... 549/61; 514/447

[56] References Cited

FOREIGN PATENT DOCUMENTS 0384314 8/1990 European Pat. Off. ............. 599/67

OTHER PUBLICATIONS

M. Wierzbicki et al., Bull. Soc. Chim. 1786–1792 (1975).
Gastineau et al., Proc. Staff Meetings of the Mayo Clinic 35, 105–111 (1960).
Skoryna, Can. Med. Assoc. J. 125 (7), 703–712 (1981).

*Primary Examiner*—Alan Siegel

[57] ABSTRACT

New divalent metal salts of 2-[N,N-di(carboxymethyl)amino]-3-cyano-4-carboxymethylthiophene-5-carboxylic acid, which can be used therapeutically especially in the treatment of bone diseases, cutaneous and vascular ageing, hepatic diseases and dental diseases.

7 Claims, 1 Drawing Sheet

DIVALENT METAL SALTS OF 2-(N-N-DI(CARBOXYMETHYL)AMINO)-3-CYANO-4-CARBOXYMETHYLTHIOPHENE-5-CARBOXYLIC ACID

The present invention provides the divalent metal salts of 2-[N,N-di(carboxymethyl)amino]-3-cyano-4-carboxymethylthiophene-5-carboxylic acid of the general formula I:

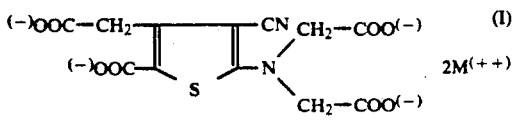

in which M represents a divalent metal, selected from the group consisting of: strontium, calcium and magnesium.

The present invention also relates to a process for the preparation of the salts of the general formula I, characterised in that the starting material used is the tetraester of formula II:

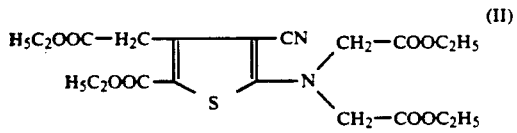

which is:

a) either heated at reflux in an aqueous alcoholic medium in the presence of sodium hydroxide solution, then hydrolysed in an acidic medium to give the acid of formula III:

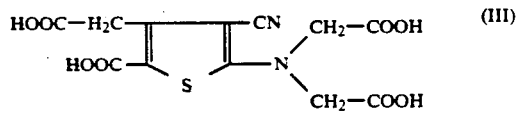

which is reacted in an aqueous medium with the hydroxide of the general formula (IV):

in which M is as defined hereinbefore;

b) or heated at reflux in a 50/50 mixture by volume of a normal sodium hydroxide solution and ethanol to obtain, after distilling off the solvents, the tetrasodium salt of formula V

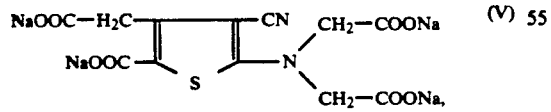

which is treated with an aqueous chloride solution of formula VI:

in which M is as defined hereinbefore;

c) or heated at reflux, in an aqueous alcoholic medium, with the hydroxide of the general formula IV defined hereinbefore.

These three methods are, in fact, merely variants of one and the same process which comprises preparing salts of formula I from the tetraester of formula II either directly (case c), or with intermediate isolation of the tetracid of formula III (case a) or the tetrasodium salt of formula V (case b).

The starting material of formula II is described in the literature (cf. M. Wierzbicki et al. Bull. Soc. Chim. (1975) pages 1786–92).

The 2-[N,N-di(carboxymethyl)amino]-3-cyano-4-carboxymethylthiophene-5-carboxylic acid of formula III is a new product which can be used as a starting material in the chemical and pharmaceutical industry, especially in the synthesis of divalent metal salts of formula I. It is thus included as such in the present invention.

The divalent metal salts of formula I have valuable therapeutic and pharmacological properties, especially remarkable anti-osteoporosis properties, as a result of which they can be used as medicaments especially in the treatment of bone diseases. They can also be used in the treatment of cutaneous and vascular ageing, hepatic diseases and dental diseases.

It is known from the prior art in this field that certain divalent metal salts can be used therapeutically especially in the treatment of bone diseases. For example, certain publications in the literature, notably Gastineau, Proc. Staff. Meetings Mayo Clinic 35, 105–11 (1960); Skoryna, Can. Med. Assoc. 125 (7), 703–712 (1981, Skoryna, Trace Subst. Environ. Health 18, 3–23 (1984) note the activity of the lactate, gluconate and carbonate of strontium in the treatment of osteoporosis.

The divalent metal salts of the present invention, apart from being new compared with the salts mentioned above, have surprisingly advantages over the latter, notably an improved bioavailability which makes it possible to administer reduced doses of the chemical in the treatment of osteoporosis.

The present invention also relates to pharmaceutical compositions containing as active ingredient one of the salts of formula I in admixture or association with an appropriate pharmaceutical excipient, such as, for example, distilled water, glucose, lactose, starch, talc, ethyl cellulose, magnesium stearate or cocoa butter.

The pharmaceutical compositions so obtained are generally in dosage form and may contain from 200 to 300 mg of active ingredient. They may be formulated as tablets, dragees, gelatin-coated pills, drinkable solutions, injectable solutions or suppositories and, depending on the case in question, may be administered orally, rectally or parenterally at a dose of from 200 to 300 mg from 2 to 4 times per day.

The following Examples illustrate the invention.

EXAMPLE 1

Synthesis of the distrontium salt of 2-[N,N-di(carboxymethyl)aminol]-3-cyano-4-carboxymethylthiophene-5-carboxylic acid:

(a) First method 1 mol (454.5 g) of the tetraethyl ester of 2-[N,N-di(carboxymethyl)amino]-3-cyano-4-carboxymethylthiophene-5-carboxylic acid is heated at reflux for approximately 3 hours in a mixture of 4 liters of ethanol, 5 l of a normal sodium hydroxide solution and 4 liters of water.

The alcohol is then distilled off; the aqueous medium is cooled and added to 1.250 ml of 4N HCl solution and the whole is precipitated with 30 liters of acetone. The sodium chloride is filtered off, the acetone is distilled off and the aqueous solution is treated with a sulphonic resin regenerated in a cycle to the (H$^{(+)}$) form until the sodium has disappeared from the solution. The whole is evaporated to dryness and the residue is recrystallised from ethyl ether then tetrahydrofuran or acetone. In this manner the pure acid is obtained, optionally crystallised with the solvent (26% of solvent in the case of tetrahydrofuran and 11% in the case of acetone) and corresponding to 240 g of pure acid (yield: 70%).

The solvated equivalent of 34.2 g (0.1 mol) of the acid is added to 660 ml of water. The organic solvent is distilled off in vacuo at 20° C. 53.14 g of strontium hydroxide.8H$_2$O are added to the aqueous solution remaining. The whole is filtered, allowed to crystallise for 24 to 48 hours, then filtered.

In this manner, the octahydrate of the distrontium salt of 2-[N,N-di(carboxymethyl)amino]-3-cyano-4-carboxymethylthiophene-5-carboxylic acid is obtained which, dried under a stream of dry air, yields the heptahydrate.

After drying the latter under reduced pressure (10 mm) at 55° C., the corresponding tetrahydrate is obtained.

The free acid can also be recrystallised directly from ethyl ether. In that case it crystallises with 4% of ether.

The physical characteristics of the products prepared in this manner are:

Acid (ether):
IR   ν(OH): 2000 and 3700 cm$^{-1}$
     ν(CN): 2220 cm$^{-1}$
     ν(CO): 1680 and 1720 cm$^{-1}$ NMR  4H - N(CH$_2$—COOH)$_2$   δ: 4.4 ppm 2H  CH$_2$ (HOOC-thiophene)   δ: 3.9 ppm octahydrate
IR   ν(CN): 2206 cm$^{-1}$
heptahydrate:
IR   ν(CN): 2210 cm$^{-1}$
     ν(COO—): 1500–1700 cm$^{-1}$
tetrahydrate:
IR   ν(CN): 2200 and 2220 cm$^{-1}$
     ν(COO—): centred at 1580 cm$^{-1}$
NMR  4H - δ: 4.4 ppm
     2H - δ: 3.9 ppm (d) Second method 1 mol of the tetraethyl ester of 2-[N,N-di(carboxymethyl)amino]-3-cyano-4-carboxymethylthiophene-5-carboxylic acid is heated at reflux for approximately 4 hours in a mixture of 4 liters of normal sodium hydroxide solution and 4 liters of ethanol.

The disappearance of the ester groups is verified by NMR. As soon as this is complete the ethanol and the majority of the water (up to a volume of 1 liter) are distilled off in vacuo in a water bath. The oil obtained is precipitated with 20 liters of ethanol. The sodium salt obtained is filtered and then dried in vacuo at 50° C.

One mol of the tetrasodium salt is dissolved in 4 liters of water. The filtered solution is added to a solution of 2 mols of strontium chloride in 4 liters of water. The whole is rapidly homogenized and then left to stand for 24 hours.

The salt formed, which is the distrontium salt, in the form of the octahydrate, of 2-[N,N-di(carboxymethyl)amino]-3-cyano-4-carboxymethylthiophene-5-carboxylic acid, is separated by filtration.

(c) Third method

A mixture of 1 mol of the tetraethyl ester of 2-[N,N-di(carboxymethyl)amino]-3-cyano-4-carboxymethylthiophene-5-carboxylic acid, two mols of strontium hydroxide, 4 liters of water and 4 liters of ethanol are refluxed for approximately one hour.

The ethanol is then distilled off, the aqueous solution is heated to 100° C., filtered hot, the residue is washed with several tens of ml of water and the octahydrate of the distrontium salt of 2-[N,N-di(carboxymethyl)amino]-3-cyano-4-carboxmethylthiophene-5-carboxylic acid so obtained is separated by filtration.

By proceeding as in the first method, the heptahydrate and tetrahydrate of the distrontium salt of 2-[N,N-di(carboxymethyl)amino]-3-cyano-4-carboxymethylthiophene-5-carboxylic acid were prepared from the octahydrate obtained according to the above second and third methods.

EXAMPLE 2

Pharmacological Study (a) Anti-resorbent properties

Anti-resorbent bone properties were demonstrated on mice calvaria according to a model based on the method described by REYNOLDS and DINGLE—A sensitive in vitro method for studying the induction and inhibition of bone resorption, Calc. Tiss. Res., 4, 339–349 (1970).

In brief, the salting out of the Ca$^{45}$ previously incorporated in the bone by subcutaneous injection into the animal is measured after culturing the calvaria for 48 hours in the presence or absence of the active ingredient.

The following results were obtained, using the distrontium heptahydrate salt of 2-[N,N-di(carboxymethyl)amino]-3-cyano-4-carboxymethylthiophene-5-carboxylic acid prepared in accordance with Example 1, in the evaluation of the bone resorption in mice calvaria:

| Concentration M | | n | control | treated | statistical significance | % variation |
|---|---|---|---|---|---|---|
| salt | Sr | | | | | |
| $5 \cdot 10^{-5}$ | $10^{-4}$ | 15 | 11.22 ± 0.33 | 11.00 ± 0.26 | NS | −1.4% ± 2.3 |
| $10^{-4}$ | $2 \cdot 10^{-4}$ | 36 | 11.63 ± 0.26 | 10.96 ± 0.20 | ** | −5.0% ± 1.6 |
| $5 \cdot 10^{-4}$ | $10^{-3}$ | 13 | 13.25 ± 0.26 | 10.95 ± 0.21 | *** | −17.1% ± 1.7 |
| $8 \cdot 10^{-4}$ | $1.6 \cdot 10^{-3}$ | 14 | 11.86 ± 0.44 | 9.35 ± 0.31 | *** | −20.9% ± 1.6 |
| $10^{-3}$ | $2 \cdot 10^{-3}$ | 14 | 14.38 ± | 10.30 ± | *** | −28.1% ± |

-continued

| Concentration M | | | | | statistical | % |
|---|---|---|---|---|---|---|
| salt | Sr | n | control | treated | significance | variation |
| | | | 0.39 | 0.34 | | 2.0 | salt = distrontium heptahydrate salt of 2-[N,N-di-(carboxymethyl)amino]-3-cyano-4-carboxymethylthiophene-5-carboxylic acid n = number of calvaria/batch average ± standard error statistical comparison by t testing for paired series
Ns: $P>0.05$; : $P<0.01$, *: $P<0.001$ These results are expressed by the graph of FIG. 1:

Figure 1:
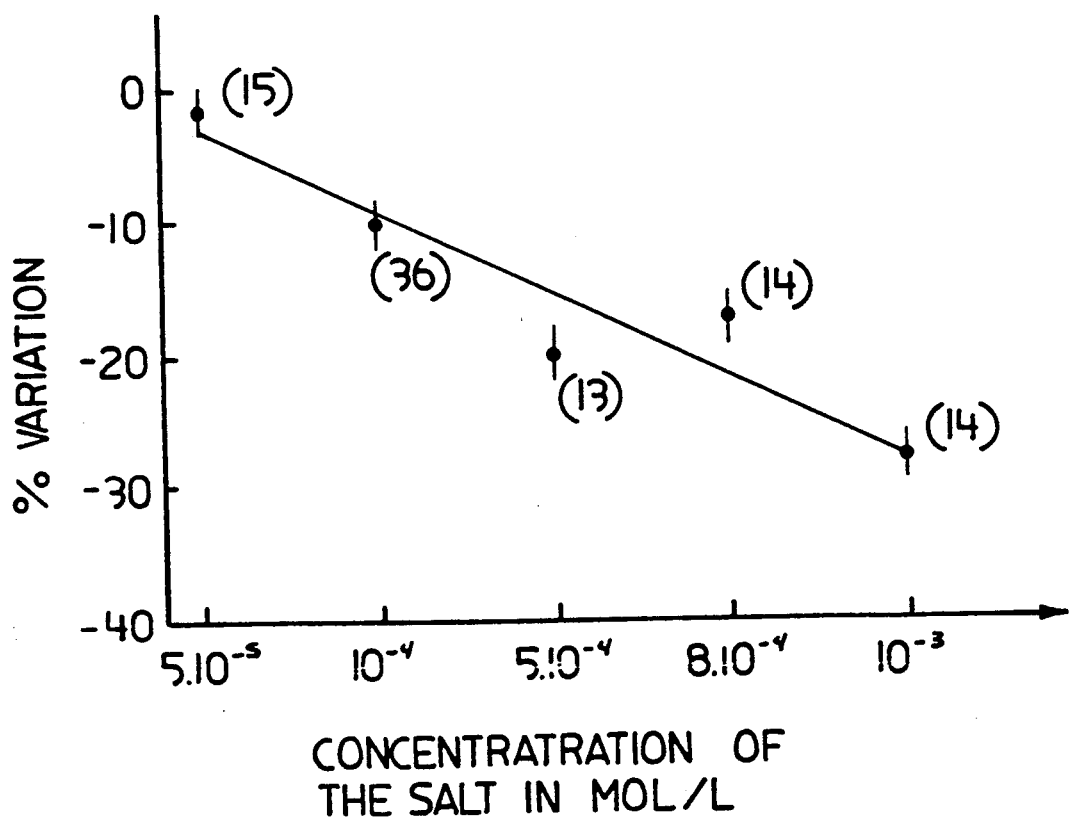
FIG. 1 expresses the foregoing results, wherein the salt is the distrontium heptahydrate salt of 2-[N,N-di(-carboxymethyl)amino]-3-cyano-4-carboxymethylthiophene-5-carboxylic acid, wherein the study was conducted on mice calvaria, in the manner described in the foregoing, wherein $y = 26.23x + 1.65$ and wherein $r = 0.988(**)$, and wherein the number n parenthesis indicates the number of calvaria studied.

Thus, ( ) number of calvaria studied average ± standard error statistical comparison by t testing for paired series
NS: $P>0.01$; : $P<0.01$; *: $P<0.001$.

The point on the graph identified by (36) has two asterisks, whereas the points on the graph identified as (13), (14), and (14) have three asterisks from the foregoing statistical standpoint.

(b) Bioavailability

This is ascertained by a study of the serum kinetics of strontium after oral administration to rats of the distrontium heptahydrate salt of the 2-[N,N-di(carboxymethyl)amino]-3-cyano-4-carboxymethylthiophene-5 -carboxylic acid prepared according to Example 1.

After a single oral administration of 50 mg/kg (in equivalents of strontium) of the distrontium heptahydrate salt of 2-[N,N-di(carboxymethyl)amino]-3-cyano-4-carboxymethylthiophene-5-carboxylic acid, the strontium is absorbed with an absolute bioavailability of 36.3%; the latter being calculated from that (taken as being 100%) of the chloride of strontium via IV.

We claim:

1. A compound selected from a divalent metal salt of 2-[N,N-di(carboxymethyl)amino]-3-cyano-4-carboxymethylthiophene-5-carboxylic acid of the formula I:

$$\begin{array}{c} (-)OOC-H_2C \\ (-)OOC \end{array} \begin{array}{c} CN \quad CH_2-COO^{(-)} \\ S \quad N \\ CH_2-COO^{(-)} \end{array} \quad 2M^{(++)} \quad (I)$$

in which M represents a divalent metal selected from the group consisting of strontium, calcium, and magnesium, and a hydrate thereof.

2. A compound of claim 1 which is:
  the distrontium salt of 2-[N,N-di(carboxymethyl)amino]-3-cyano-4-carboxymethylthiophene-5-carboxylic acid, in the form of the octahydrate, the heptahydrate or the tetrahydrate.

3. 2-[N,N-di(carboxymethyl)amino]-3-cyano-4-carboxymethylthiophene-5-carboxylic acid.

4. A pharmaceutical composition, useful for the treatment of osteoporosis, containing, as active ingredient, an effective amount of a salt of claim 1 together with an appropriate carrier.

5. A method for treating a living animal afflicted with osteoporosis comprising the step of administering to the said living animal an amount of a compound of claim 1 which is effective for alleviation of the said condition.

6. Pharmaceutical compositions, useful for the treatment of osteoporosis, containing, as active ingredient, an effective amount of a salt of claim 2 together with an appropriate carrier.

7. A method for treating a living animal body afflicted with osteoporosis comprising the step of administering to the said living animal an amount of a compound of claim 2 which is effective for the alleviation of the said condition.

* * * * *

UNITED STATES PATENT AND TRADEMARK OFFICE
CERTIFICATE OF CORRECTION

PATENT NO. : 5,128,367

Page 1 of 2

DATED : Jul. 7, 1992

INVENTOR(S) : Michel Wierzbicki, Jacqueline Bonnet, Martine Brisset, Yannis Tsouderos It is certified that error appears in the above-identified patent and that said Letters Patent is hereby corrected as shown below:

Title Page [54], 2nd line; "(N-N-DI(CARBOXYMETHYL) AMINO)" should read --[N,N-DI(CARBOXYMETHYL)AMINO]--

Title Page, [75] Inventors: "Wierzbicki, Etang" should read -- Wierzbicki, L'Etang --.

Title Page, 2nd column, under "Primary Examiner" insert -- Attorney, Agent, or Firm—Gordon W. Hueschen --.

Title Page, [57] ABSTRACT, line 2; move the closing parenthesis ")" at the beginning of line 2 to the end of line 1 and insert before the hyphen.

Column 2, approximately line 34; "surprisingly should read -- surprising --.

Column 4, line 15/16; move the closing parenthesis ")" at the beginning of line 28 to the end of line 27 and insert before the hyphen.

Column 4, line 27/28; move the closing parenthesis ")" at the beginning of line 28 to the end of line 27 and insert before the hyphen.

Column 5, approximately line 26; "n" should read -- in --.
(R&A 11-15-92, P. 1)

UNITED STATES PATENT AND TRADEMARK OFFICE
CERTIFICATE OF CORRECTION

PATENT NO. : 5,128,367

DATED : Jul. 7, 1992

INVENTOR(S) : Michel Wierzbicki, Jacqueline Bonnet, Martine Brisset, Yannis Tsouderos It is certified that error appears in the above-identified patent and that said Letters Patent is hereby corrected as shown below:

Column 5, approximately line 41; move the closing parenthesis ")" at the beginning of line 41 to the end of line 40 and insert before the hyphen.

Column 6, line 25; move the closing parenthesis ")" at the beginning of line 25 to the end of line 24 and insert before the hyphen.

Signed and Sealed this

Thirty-first Day of August, 1993

BRUCE LEHMAN

*Attest:*

*Attesting Officer*          *Commissioner of Patents and Trademarks*